United States Patent [19]

Shichman

[11] Patent Number: 5,104,383

[45] Date of Patent: Apr. 14, 1992

[54] TROCAR ADAPTER SEAL AND METHOD OF USE

[75] Inventor: Daniel Shichman, Trumbull, Conn.

[73] Assignee: United States Surgical Corporation, Norwalk, Conn.

[21] Appl. No.: 673,848

[22] Filed: Mar. 20, 1991

Related U.S. Application Data

[63] Continuation of Ser. No. 422,635, Oct. 17, 1989, abandoned.

[51] Int. Cl.$^5$ .............................................. A61M 5/178
[52] U.S. Cl. ........................................ 604/167; 604/49; 604/256
[58] Field of Search ............... 604/164, 165, 167, 264, 604/268, 49, 51, 256; 606/184–185

[56] References Cited

U.S. PATENT DOCUMENTS

| 3,994,287 | 11/1976 | Turp et al. |
| 4,000,739 | 1/1977 | Stevens. |
| 4,177,814 | 12/1979 | Knepshield et al. |
| 4,392,485 | 7/1983 | Hiltebrandt. |
| 4,601,710 | 7/1986 | Moll. |
| 4,654,030 | 3/1987 | Moll et al. |
| 4,673,393 | 6/1987 | Suzuki et al. | 604/167 |
| 4,705,511 | 11/1987 | Kocak | 604/282 |
| 4,929,235 | 5/1990 | Merry et al. | 604/167 |
| 4,960,412 | 10/1990 | Fink | 604/167 |

FOREIGN PATENT DOCUMENTS

| 0051718 | 5/1982 | European Pat. Off. |
| 0113520 | 7/1984 | European Pat. Off. |
| 7145806 | 6/1972 | Fed. Rep. of Germany. |
| 3042229 | 5/1982 | Fed. Rep. of Germany | 604/167 |
| 7527593 | 4/1976 | France. |
| 1482857 | 8/1977 | United Kingdom. |

OTHER PUBLICATIONS

Information booklet for Auto Suture Surgiport Disposable Surgical Trocar and Sleeve, 1988.
Richard Wolf Product Catalog, p. I-86.
Information Booklet for Auto Suture ® Surgiport ® Disposable Surgical Trocar and Sleeve.

*Primary Examiner*—C. Fred Rosenbaum
*Assistant Examiner*—C. Maglione

[57] ABSTRACT

An adapter seal for use with a cannula assembly is provided. The adapter seal gives a surgeon increased flexibility in performing endoscopic procedures by allowing the use of variously sized instruments through a single cannula. The adapter seal is preferably provided with a stabilizer plate to limit the eccentric movement of an instrument relative to the seal, which may inadvertently release the gaseous seal.

10 Claims, 5 Drawing Sheets

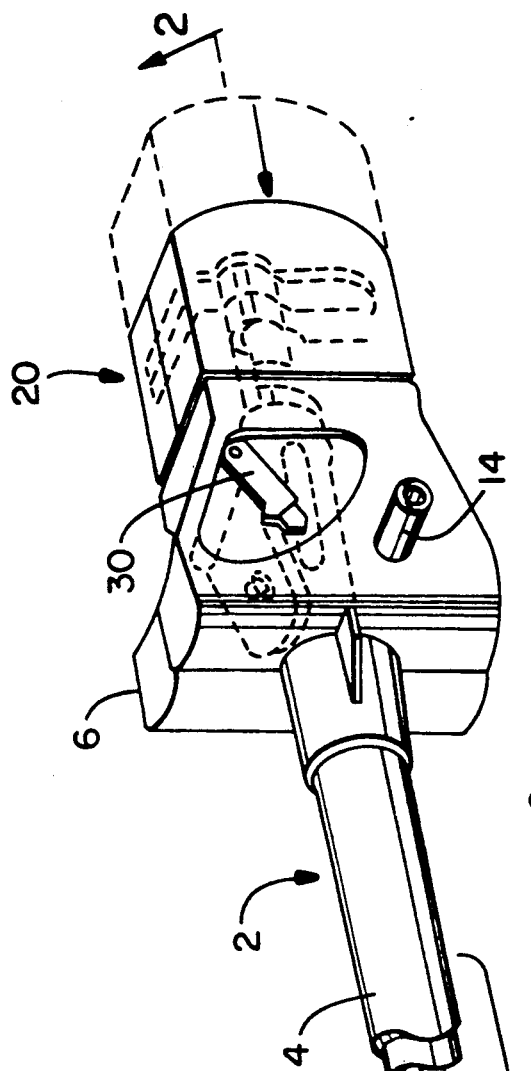
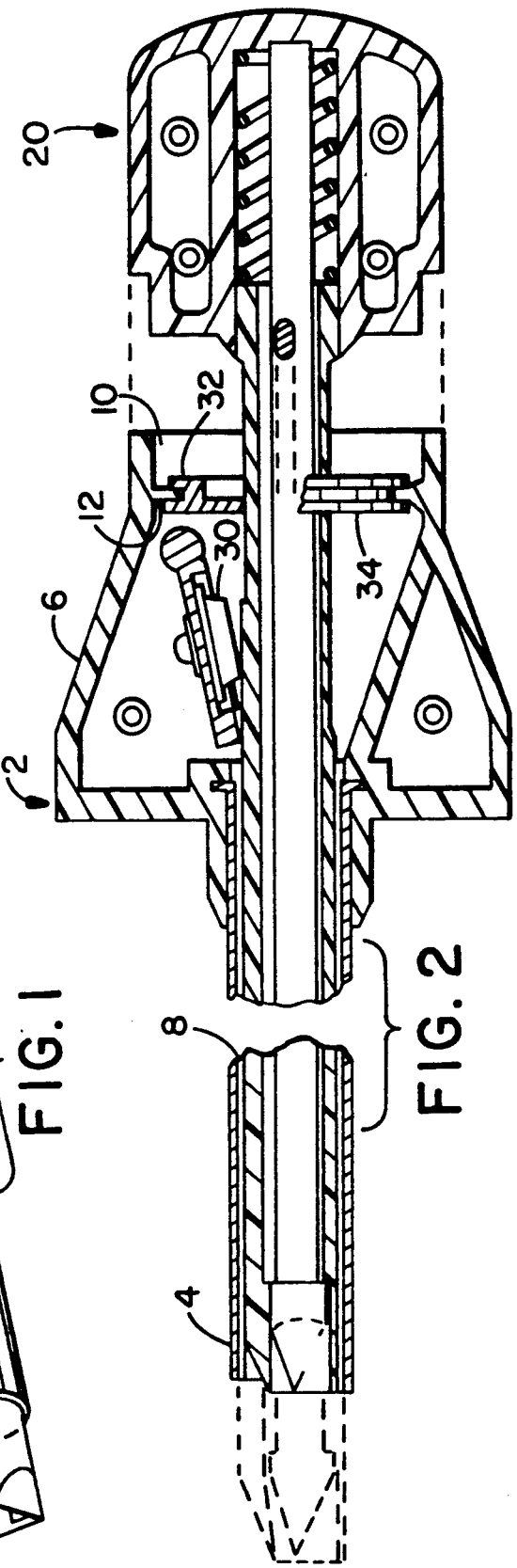

TROCAR ADAPTER SEAL AND METHOD OF USE

This is a continuation of co-pending application Ser. No. 422,635, filed on Oct. 17, 1989 now abandoned.

BACKGROUND OF THE INVENTION

1. Technical Field

The present invention relates to an adapter seal for use with a cannula assembly and to a method for performing surgical procedures using the adapter seal.

2. Description of the Prior Art

Insufflatory surgery involves filling a body cavity with a pressurized gas to maintain the cavity under a certain predetermined pressure. One way of performing the surgery is by first puncturing the skin in a desired body cavity region with a needle. The needle includes a stylet which introduces an insufflation gas into the body cavity to inflate it.

A trocar is then used to puncture the body cavity. The trocar is inserted through a cannula or sheath, which cannula partially enters the body cavity through the incision made by the trocar. The trocar then be removed from the cannula, and surgical instruments may be inserted through the cannula to perform various endoscopic procedures, e.g., an elongated endoscope may be inserted through the cannula to view the anatomical cavity.

Various types of cannula or trocar assemblies are provided with valves for maintaining a certain gas pressure in the cavity when the trocar or other surgical instrument is removed from the cannula. Trocar assemblies are available as disposable or reusable units, the latter units being resterilized between successive operative procedures.

For example, U.S. Pat. Nos. 4,601,710 to Moll and 4,654,030 to Moll et al, disclose trocar assemblies which include an elongate trocar obturator having a piercing tip at its front end and an elongate trocar tube or cannula in which the trocar obturator is housed. As shown in the '030 patent, a flapper valve may be employed to close off the cannula passage after the trocar obturator or other instrument has been withdrawn.

A gasket may also be employed to ensure a seal between the trocar assembly and an instrument inserted therein. U.S. Pat. No. 4,000,739 to Stevens, for example, teaches a hemostasis cannula having a pair of juxtaposed gaskets mounted in the passageway to the cannula, the first having a round hole and the second a Y-shaped slit. U.S. Pat. No. 3,994,287 to Turp et al. describes a trocar assembly which involves a flexible insulating ring received in a flange and a collar which retains the flexible ring in the flange. The flexible ring is allowed to flex as an instrument is inserted into the cannula and provides a seal with the instrument to prevent gas leakage.

Endoscopic surgical procedures employ a variety of surgical instruments, e.g., endoscopes, biopsy forceps, bipolar forceps, coagulation probes, etc. Due to the non-invasive nature of endoscopic procedures, endoscopy is a preferred surgical approach when possible. As such, additional instruments and accessories for use in endoscopic procedures are being introduced at a rapid pace. These instruments have differing sizes, for example, some instruments have a cross-sectional diameter in their elongate regions on the order of 5 mm whereas others have a diameter of 10 mm or larger. In recognition of this instrument variability, cannulas are available in different inner diameters. Commercially available trocars offer having a broad range of inner diameters, ranging from 3 to 12 mms (e.g., 3, 5, 7, 8, 10, 11, and 12 mm sizes).

Despite the availability of trocar assemblies having cannulas of various sizes, it is both inconvenient and impractical for a surgeon to insert multiple cannulas into a patient to accommodate the various instrument sizes employed in a given surgical procedure. This greatly restricts the flexibility available to surgeons in performing endoscopic procedures. For example, the use of a 5 mm instrument in a 10 mm cannula is not possible because a gas seal would not exist between the trocar assembly and the instrument. Similarly, the use of a 10 mm instrument in a 5 mm cannula is impossible because the instrument simply doesn't fit. It has therefore been necessary heretofore for a surgeon to effect multiple cannula placements to accommodate the use of instruments of varying size.

SUMMARY OF THE INVENTION

It is an object of the present invention to provide an adapter seal for use with a cannula assembly which permits the use of variously sized instruments with the cannula assembly.

It is another object of the present invention to provide an adapter seal which may be securely and conveniently received by the cannula assembly.

It is further object to provide an adapter seal which provides an effective seal with an endoscopic surgical instrument.

It is yet another object of the invention to provide a method whereby surgical instruments of differing sizes may be used endoscopically through a single cannula.

These and other objects of the invention are realized by an adapter seal which comprises an adapter plate having a circular aperture for receiving a surgical instrument. The adapter plate is sized and dimensioned to be received by a cannula assembly, typically by a housing integrally attached to the cannula. The circular aperture is sized to cooperate with an instrument having an elongate portion of reduced cross section to the cross section of the cannula through which it is to pass. For example, the adapter seal of the present invention may be dimensioned for use with a 10 mm cannula assembly and have an aperture sized to cooperate with a 5 mm instrument.

The adapter seal of the invention also preferably includes a stabilizer plate of relatively rigid material, the stabilizer plate having an orifice of larger diameter than the aperture in the adapter plate. The stabilizer plate cooperates with the adapter plate to provide rigidity thereto. The orifice in the stabilizer plate is sized to cooperate with and restrict excessive eccentric motion of the instrument relative to the adapter seal which could break the gaseous seal.

In use, a cannula, e.g., a 10 mm cannula, may be inserted into a body cavity in a conventional manner, and the sharp-tipped trocar removed therefrom. At this point, the surgeon is only in a position to endoscopically employ instruments having an elongate portion having an other diameter of about 10 mm. Should the surgeon desire to insert an instrument of smaller size, e.g., a 5 mm instrument, the adapter seal of the present invention is positioned such that the elongate portion of the 5 mm instrument may be inserted through the aperture in the adapter plate and into the 10 mm cannula. The adapter plate cooperates with the cannula assembly and with the 5 mm instrument to provide a gaseous seal. The surgeon may subsequently use larger or smaller instruments by removing the 5 mm adapter seal and positioning a second adapter seal of different aperture size or by using the 10 mm cannula with a 10 mm instrument. The surgeon is thus provided with tremendous flexibility in his selection and use of surgical instruments in endoscopic procedures.

BRIEF DESCRIPTION OF THE DRAWINGS

The present invention will become more apparent from the following detailed description taken in conjunction with the accompanying drawings in which:

FIG. 1 is an isometric view of a cannula assembly with which the adapter seal of the present invention may be used, the cannula assembly having a trocar assembly mounted therein;

FIG. 2 is a section view of the cannula assembly and trocar assembly shown in FIG. 1, taken along line 2—2 of FIG. 1;

DETAILED DESCRIPTION OF THE INVENTION

Figure 3:
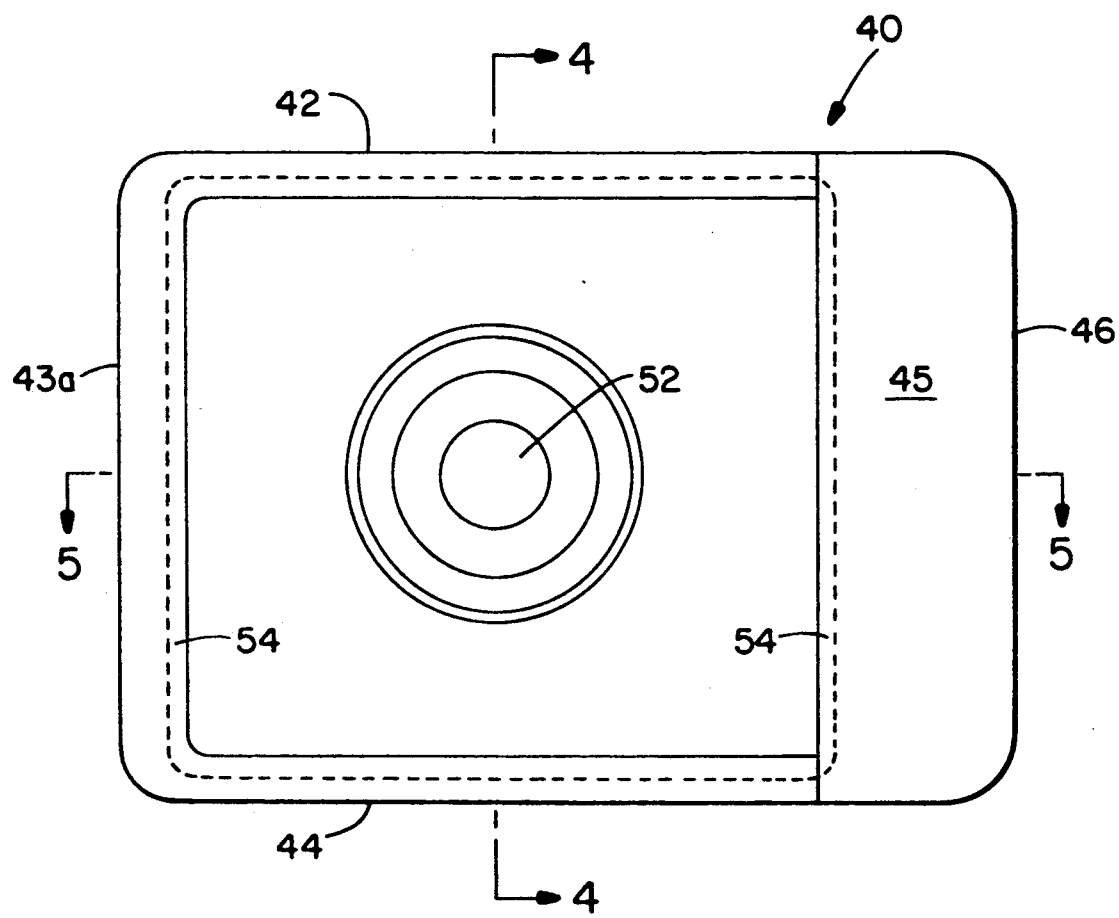
FIG. 3 is a bottom view of an adapter seal of the present invention.

Referring initially to FIGS. 1 and 2 of the drawings, it will be seen that a trocar assembly 2 used in connection with insufflatory and/or endoscopic surgical procedures basically includes a cannula 4 and a housing 6 mounted on one end of cannula 4. Cannula 4 is formed as an elongated sleeve having opposite proximate and distal open ends, and thus defines a cannula passage 8 in its interior. The inner diameter of cannula 4 determines the maximum size instrument which may be inserted through trocar assembly 2 into a body cavity. Typical cannula diameters are 3 mm, 5 mm, 7 mm, 8 mm, 10 mm, 11 mm and 12 mm, although cannula diameters may be manufactured as desired. Cannula 4 may formed from a stainless steel or other rigid material.

The housing 6 of the cannula assembly is rigidly secured to the proximate end of the cannula 4. It has an open interior for mounting other components of the cannula assembly, and has a rear opening 10 defined by a circular flange 12 extending inwardly of the housing, which opening 10 is situated coaxially with the cannula 4.

The cannula assembly 2, with its cannula 4 and its housing 6, is adapted to receive surgical instruments through the opening 10 in its housing. An example of such an instrument is the trocar assembly 20 shown in FIGS. 1 and 2 of the drawings, the trocar assembly cooperating with the rear side of the housing 6. Trocar assemblies of the type shown in FIGS. 1 and 2 are well known in the art.

Cannula assembly 2 is also generally provided with a valve which opens to allow a surgical instrument, such as trocar assembly 20, to be inserted through cannula 4, and which closes when the surgical instrument has been withdrawn, in order to maintain gas pressure in the body cavity which is generally insufflated. The cannula assembly 2 shown in FIGS. 1 and 2 is provided with a flapper valve 30 which engages a valve seat 32. A circular flange 12 is provided in housing 6 to cooperate with recess 34 in valve seat 32, thereby securing valve seat 32 in place.

Figure 4:
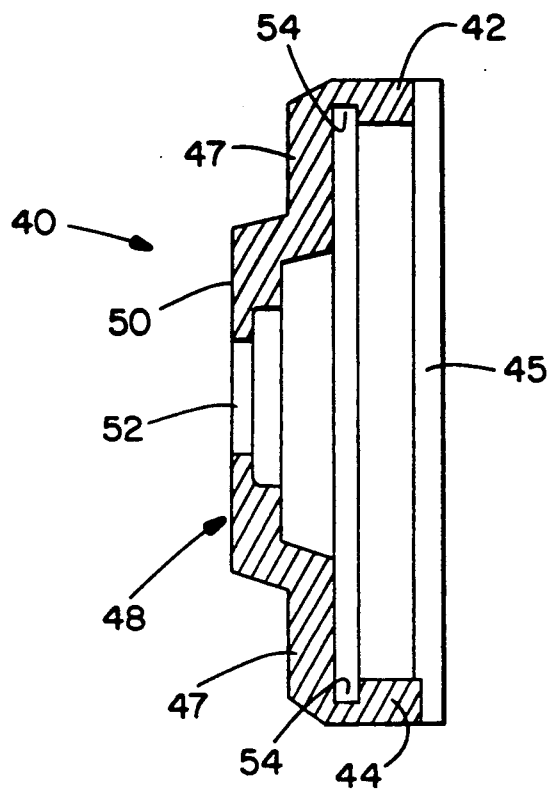
FIG. 4 is a cross-sectional side view of the adapter seal of the invention, taken along line 4—4 of FIG. 3.
Figure 5:
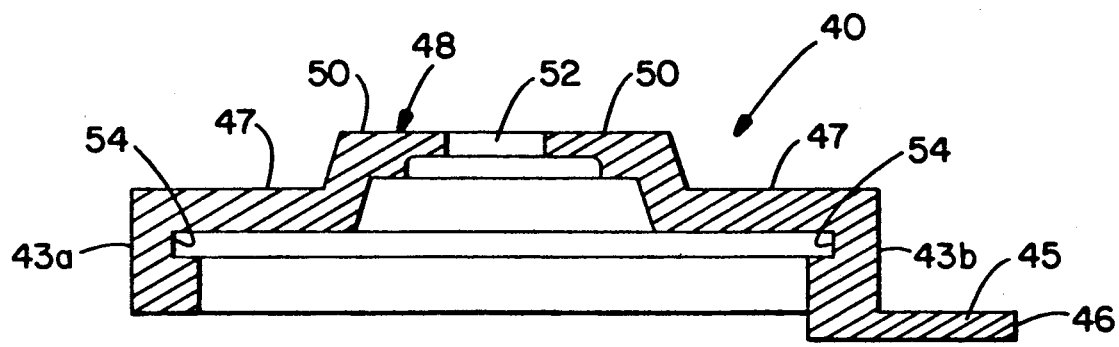
FIG. 5 is a cross-sectional top view of the adapter seal, taken along line 5—5 of FIG. 3.

Referring to FIGS. 3–6, an adapter seal 40 is provided which includes top wall 42, side walls 43a and 43b, bottom wall 44, and extension flap 45 having a flap wall 46. Referring particularly to FIGS. 4 and 5, walls 42, 43a and 43b and 44 are integral with abutment face 47. A cylindrical extension 48 extends from abutment face 47, ending in circular face 50.

Figure 6A:
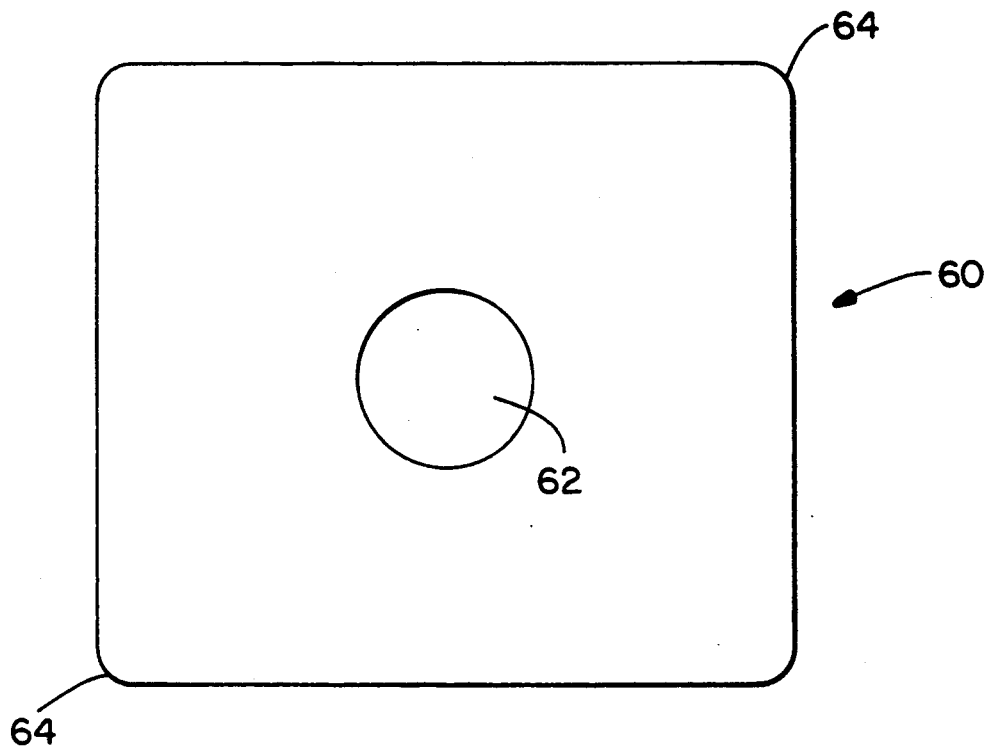
FIGS. 6a and 6b are a front and cross-sectional side view of the stabilizer plate of the invention, respectively.
Figure 6B:
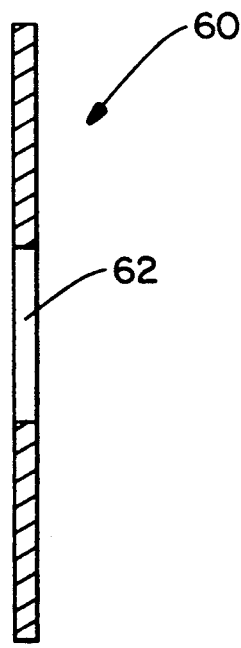

An aperture 52 extends through abutment face 50. The diameter of aperture 52 increases as the aperture extends toward the region bounded by walls 42 and 44. The practical effect of the varied diameter is to provide increased flexibility to aperture 52 due to reduced wall thickness in the aperture region by circular face 50. This increased flexibility provides for improved sealing when a surgical instrument (not pictured) is passed through aperture 52. A slot 54 extends around the periphery of adapter seal 40, as shown in phantom in FIG. 3. Slot 54 is adapted to receive a stabilizer plate 60, as shown in FIGS. 6a and 6b. Stabilizer plate 60 has an orifice 62 at its center, the size of orifice 62 being larger, e.g., 10 to 50% larger, than the diameter of aperture 52 in adapter seal 40. Stabilizer plate 60 is typically manufactured from a resilient plastic material such as an ABS polymer. Stabilizer plate 60 is also typically provided with rounded edges 64 to facilitate its placement in peripheral slot 54 of adapter seal 40.

The adapter seal of the present invention preferably includes a stabilizer plate 60 so as to improve the reliability of the gaseous seal with a surgical instrument inserted through aperture 52 of adapter seal 40. To impart flexibility to cylindrical extension 48, it is generally necessary to fabricate the adapter seal from an elastomeric material. This flexibility also makes it possible for the surgeon to manipulate the instrument at extreme angles relative to the adapter seal, thereby jeopardizing the gaseous seal. However, stabilizer plate 60, and particularly the perimeter of orifice 62, restricts the freedom of movement of the instrument relative to adapter seal 40. This restriction helps to ensure that a gaseous seal will be maintained by engagement of circular face 50 with the instrument.

Figure 7:
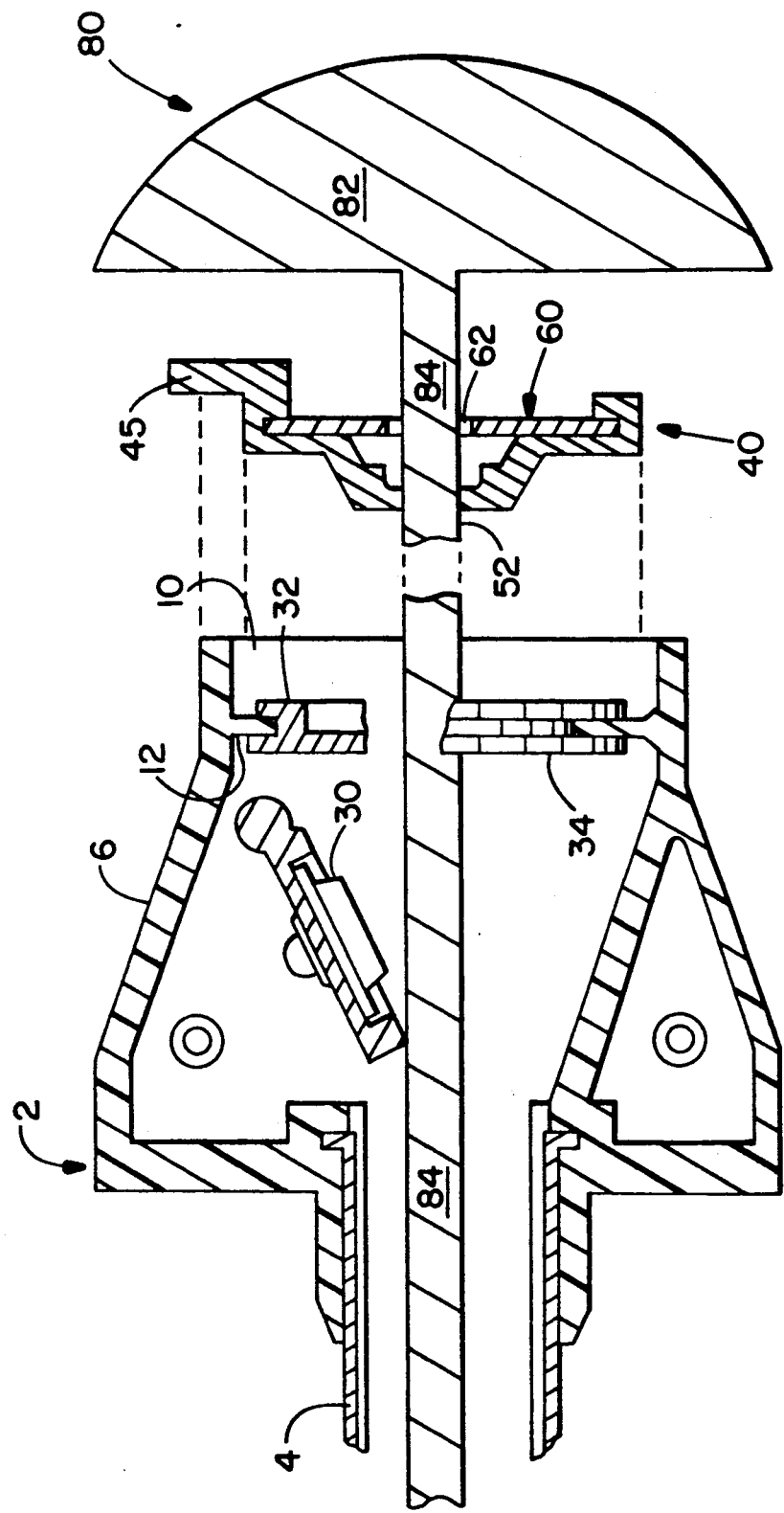
FIG. 7 is an exploded cross-sectional view of the adapter seal, the rear portion of a cannula assembly, and a surgical instrument, according to the present invention.

Turning to FIG. 7, adapter seal 40 with stabilizer plate 60 is positioned within rear opening 10 of cannula assembly. Extension flap 45 of adapter seal 40 abuts against the rearward extension of housing 6, thereby axially positioning adapter seal 40. The walls 42, 43a and 43b, and 44 of adapter seal 40 are in frictional engagement with the inner wall of opening 10, and provide a gaseous seal therewith.

A surgical instrument 80 having a handle 82 and an elongated shaft 84 is inserted through orifice 62 in stabilizer plate 60, orifice 52 in adapter seal 40, and valve seat 32 (deflecting flapper valve 30 radially upward) so as to extend into cannula 4. Adapter seal 40 provides a gaseous seal with elongated shaft 84, thereby sealing the body cavity from communication with the external environment. Thus, despite the difference in diameter between the cannula assembly 2, and more particularly the valve seat 32, and the shaft 84, cannula assembly 2 may be effectively employed in an endoscopic procedure utilizing surgical instrument 80.

As is readily apparent, the surgeon is also free to remove instrument 80 from cannula assembly 2, remove adapter seal 40 from opening 10, and again use cannula assembly 2 in conjunction with an instrument of the size for which it was designed. Alternatively, an adapter seal having an aperture of larger or smaller diameter may be inserted in opening 10 in place of original adapter seal 40. Thus, a vast array of surgical instruments may be employed by the surgeon using a single cannula assembly 2.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

I claim:

1. A method for performing an endoscopic procedure comprising:
   a) inserting a cannula assembly into a body cavity;
   b) placing an adapter seal in said cannula assembly, said adapter seal comprising an adapter plate having an adapter plate sealing aperture and a stabilizer plate, said adapter seal removably engaging and cooperating with said cannula assembly to provide a gaseous seal along the periphery of said adapter seal;
   c) inserting a first surgical instrument having a first diameter through said aperture into said cannula assembly;
   d) removing said adapter seal from said cannula assembly and continuing said endoscopic procedure with a second instrument of larger size.

2. The method of claim 1, wherein said adapter seal provides a gaseous seal with an elongate portion of said surgical instrument.

3. The method of claim 1, wherein said adapter plate sealing aperture is of reduced cross section relative to the inner diameter of the cannula assembly.

4. The method of claim 1, wherein said cannula assembly comprises a cannula having an inner diameter of about 10 mm and said adapter plate sealing aperture has a diameter of about 5 mm.

5. The method of claim 1, wherein said adapter plate is fabricated from a flexible plastic material.

6. The method of claim 1, wherein said stabilizer plate has an orifice for receiving said first and second surgical instruments.

7. The method of claim 6, wherein said adapter plate has a slot which extends around its periphery and said stabilizer plate is received therein.

8. The method of claim 6, wherein said stabilizer plate orifice is from 10 to 50% larger than said adapter plate sealing aperture.

9. The method of claim 1, wherein said stabilizer plate is fabricated from a rigid plastic material.

10. The method of claim 1, wherein said adapter seal is placed in frictional engagement with said cannula assembly.

* * * * *